United States Patent
Plumptre

(10) Patent No.: US 11,654,243 B2
(45) Date of Patent: *May 23, 2023

(54) INNER HOUSING FOR A DRUG DELIVERY DEVICE

(71) Applicant: SANOFI-AVENTIS DEUTSCHLAND GMBH, Frankfurt am Main (DE)

(72) Inventor: David Plumptre, Worcestershire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 549 days.

This patent is subject to a terminal disclaimer.

(21) Appl. No.: 16/530,125

(22) Filed: Aug. 2, 2019

(65) Prior Publication Data

US 2019/0351145 A1   Nov. 21, 2019

Related U.S. Application Data

(63) Continuation of application No. 14/812,133, filed on Jul. 29, 2015, now Pat. No. 10,391,254, which is a (Continued)

(30) Foreign Application Priority Data

Jul. 10, 2009  (EP) .................................. 09009042

(51) Int. Cl.
   *A61M 5/315*  (2006.01)
   *A61M 5/31*   (2006.01)

(52) U.S. Cl.
   CPC .... *A61M 5/31543* (2013.01); *A61M 5/31541* (2013.01); *A61M 5/31551* (2013.01);
   (Continued)

(58) Field of Classification Search
   CPC .......... A61M 5/31543; A61M 5/31541; A61M 5/31551; A61M 5/31585;
   (Continued)

(56) References Cited

U.S. PATENT DOCUMENTS

| 533,575 A | 2/1895 | Wilkins |
| 3,302,462 A | 2/1967 | Pursell |

(Continued)

FOREIGN PATENT DOCUMENTS

| CA | 2138528 | 12/1998 |
| CA | 2359375 | 7/2000 |

(Continued)

OTHER PUBLICATIONS

"Pen-injectors for medical use—Part 1: Pen-injectors—Requirements and test methods," International Standard, reference No. ISO 11608-1:2000(E), first edition Dec. 15, 2000, 32 pages.

(Continued)

*Primary Examiner* — Theodore J Stigell
(74) *Attorney, Agent, or Firm* — Fish & Richardson P.C.

(57) ABSTRACT

A dose setting mechanism for a drug delivery device is disclosed. The mechanism comprises an outer housing and an inner housing having an external groove. The inner housing guides a driver to dispense a set dose. A dial sleeve is disposed between the outer and inner housing and is rotatably engaged with the inner housing. When a dose is set, the dial sleeve is rotated and translates away from both the outer housing and the inner housing.

19 Claims, 12 Drawing Sheets

Related U.S. Application Data continuation of application No. 13/375,186, filed as application No. PCT/EP2010/057456 on May 28, 2010, now Pat. No. 9,125,993.

(60) Provisional application No. 61/182,818, filed on Jun. 1, 2009.

(52) U.S. Cl.
CPC . *A61M 5/31585* (2013.01); *A61M 2005/3126* (2013.01); *A61M 2205/27* (2013.01)

(58) Field of Classification Search
CPC ...... A61M 2005/3126; A61M 2205/27; A61M 5/31548; A61M 5/31533
See application file for complete search history.

(56) References Cited

U.S. PATENT DOCUMENTS

| | | | |
|---|---|---|---|
| 3,815,785 A * | 6/1974 | Gilmont | A61M 3/00 |
| | | | D24/114 |
| 4,865,591 A | 9/1989 | Sams | |
| 5,092,842 A | 3/1992 | Bechtold et al. | |
| 5,226,895 A | 7/1993 | Harris | |
| 5,226,896 A * | 7/1993 | Harris | A61M 5/31551 |
| | | | 604/209 |
| 5,279,586 A | 1/1994 | Balkwill | |
| 5,304,152 A | 4/1994 | Sams | |
| 5,320,609 A | 6/1994 | Haber et al. | |
| 5,378,233 A | 1/1995 | Haber et al. | |
| 5,383,865 A | 1/1995 | Michel | |
| 5,391,157 A | 2/1995 | Harris et al. | |
| 5,423,752 A | 6/1995 | Haber et al. | |
| 5,480,387 A | 1/1996 | Gabriel et al. | |
| 5,505,704 A | 4/1996 | Pawelka et al. | |
| 5,514,097 A | 5/1996 | Knauer | |
| 5,582,598 A | 12/1996 | Chanoch | |
| 5,584,815 A | 12/1996 | Pawelka et al. | |
| 5,591,136 A | 1/1997 | Gabriel | |
| 5,626,566 A | 5/1997 | Petersen et al. | |
| 5,674,204 A | 10/1997 | Chanoch | |
| 5,688,251 A | 11/1997 | Chanoch | |
| 5,725,508 A | 3/1998 | Chanock et al. | |
| 5,792,117 A | 8/1998 | Brown | |
| 5,807,346 A | 9/1998 | Frezza | |
| 5,820,602 A | 10/1998 | Kovelman et al. | |
| 5,851,079 A | 12/1998 | Horstman et al. | |
| 5,921,966 A | 7/1999 | Bendek et al. | |
| 5,957,896 A | 9/1999 | Bendek et al. | |
| 5,961,495 A | 10/1999 | Walters et al. | |
| 6,004,297 A | 12/1999 | Steenfeldt-Jensen et al. | |
| 6,090,080 A | 7/2000 | Jost et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,562,006 B1 | 5/2003 | Hjertman et al. | |
| 6,613,023 B2 | 9/2003 | Kirchhofer et al. | |
| 6,663,602 B2 | 12/2003 | Moller | |
| 6,699,224 B2 | 3/2004 | Kirchhofer et al. | |
| 6,899,698 B2 | 5/2005 | Sams | |
| 6,932,794 B2 | 8/2005 | Giambattista et al. | |
| 6,936,032 B1 | 8/2005 | Bush, Jr. et al. | |
| 7,169,132 B2 | 1/2007 | Bendek et al. | |
| 7,241,278 B2 | 7/2007 | Moller | |
| 7,678,084 B2 | 3/2010 | Judson et al. | |
| 7,850,662 B2 | 12/2010 | Veasey et al. | |
| 8,070,727 B2 | 12/2011 | Veasey et al. | |
| 8,187,233 B2 | 5/2012 | Harms et al. | |
| 9,125,993 B2 * | 9/2015 | Plumptre | A61M 5/31543 |
| 10,391,254 B2 * | 8/2019 | Plumptre | A61M 5/31543 |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0097883 A1 | 5/2004 | Roe | |
| 2004/0127858 A1 | 7/2004 | Bendek et al. | |
| 2004/0162528 A1 | 8/2004 | Horvath et al. | |
| 2004/0186437 A1 | 9/2004 | Frenette et al. | |
| 2004/0210199 A1 | 10/2004 | Atterbury et al. | |
| 2004/0236285 A1 | 11/2004 | Fisher et al. | |
| 2004/0267207 A1 | 12/2004 | Veasey et al. | |
| 2005/0004529 A1 * | 1/2005 | Veasey | A61M 5/31585 |
| | | | 604/209 |
| 2005/0113765 A1 | 5/2005 | Veasey et al. | |
| 2005/0137571 A1 | 6/2005 | Hommann | |
| 2006/0153693 A1 | 7/2006 | Fiechter et al. | |
| 2006/0258988 A1 * | 11/2006 | Keitel | A61M 5/31551 |
| | | | 604/181 |
| 2007/0016143 A1 | 1/2007 | Miller et al. | |
| 2007/0021718 A1 | 1/2007 | Burren et al. | |
| 2007/0093761 A1 | 4/2007 | Veasey et al. | |
| 2008/0027397 A1 | 1/2008 | DeRuntz et al. | |
| 2008/0077095 A1 | 3/2008 | Kirchhofer | |
| 2008/0208123 A1 | 8/2008 | Hommann | |
| 2009/0227955 A1 | 9/2009 | Hirschel et al. | |
| 2009/0227959 A1 | 9/2009 | Hirschel et al. | |
| 2009/0275916 A1 | 11/2009 | Harms et al. | |

FOREIGN PATENT DOCUMENTS

| | | |
|---|---|---|
| CN | 1277558 | 12/2000 |
| CN | 1816363 | 8/2006 |
| DE | 9301334 | 4/1993 |
| DE | 19730999 | 12/1998 |
| DE | 29818721 | 3/2000 |
| DE | 102005063311 | 8/2006 |
| DE | 102005060928 | 6/2007 |
| DE | 102006038123 | 2/2008 |
| DE | 102007026083 | 11/2008 |
| EA | 007402 | 10/2006 |
| EA | 007763 | 12/2006 |
| EP | 0496141 | 7/1992 |
| EP | 0608343 | 12/1997 |
| EP | 0897728 | 2/1999 |
| EP | 0897729 | 2/1999 |
| EP | 0937471 | 8/1999 |
| EP | 0937472 | 8/1999 |
| EP | 0937476 | 8/1999 |
| EP | 1541185 | 6/2005 |
| EP | 1776975 | 4/2007 |
| EP | 1923084 | 5/2008 |
| GB | 2443390 | 5/2008 |
| JP | 1995-500039 | 1/1995 |
| JP | 1996-000730 | 1/1995 |
| JP | 2002-501790 | 1/2002 |
| JP | 2006-519074 | 8/2006 |
| JP | 2006-519078 | 8/2006 |
| JP | 2006-522630 | 10/2006 |
| JP | 2008-529687 | 8/2008 |
| JP | 2009-500095 | 1/2009 |
| WO | WO 92/18180 | 10/1992 |
| WO | WO 93/07922 | 4/1993 |
| WO | WO 93/24160 | 12/1993 |
| WO | WO 96/23973 | 8/1996 |
| WO | WO 96/39214 | 12/1996 |
| WO | WO 97/10864 | 3/1997 |
| WO | WO 99/03520 | 1/1999 |
| WO | WO 99/38554 | 8/1999 |
| WO | WO 01/10484 | 2/2001 |
| WO | WO 01/19434 | 3/2001 |
| WO | WO 02/30495 | 4/2002 |
| WO | WO 2002/030495 | 4/2002 |
| WO | WO 02/092153 | 11/2002 |
| WO | WO 03/080160 | 10/2003 |
| WO | WO 2004/020028 | 3/2004 |
| WO | WO 2004/064902 | 8/2004 |
| WO | WO 2004/078226 | 9/2004 |
| WO | WO 2004/078241 | 9/2004 |
| WO | WO 2004/078242 | 9/2004 |
| WO | WO 2004/078293 | 9/2004 |
| WO | WO 2004/082748 | 9/2004 |
| WO | WO 2004/089450 | 10/2004 |

(56) References Cited

FOREIGN PATENT DOCUMENTS

| WO | WO 2005/018721 | 3/2005 |
|---|---|---|
| WO | WO 2005/021072 | 3/2005 |
| WO | WO 2005/044346 | 5/2005 |
| WO | WO 2005/123159 | 12/2005 |
| WO | WO 2006/024461 | 3/2006 |
| WO | WO 2006/058883 | 6/2006 |
| WO | WO 2006/079481 | 8/2006 |
| WO | WO 2006/084876 | 8/2006 |
| WO | WO 2006/089767 | 8/2006 |
| WO | WO 2006/114395 | 11/2006 |
| WO | WO 2006/125328 | 11/2006 |
| WO | WO 2007/006662 | 1/2007 |
| WO | WO 2007/017052 | 2/2007 |
| WO | WO 2007/067889 | 6/2007 |
| WO | WO 2008/019514 | 2/2008 |
| WO | WO 2008/031235 | 3/2008 |
| WO | WO 2008/074897 | 6/2008 |
| WO | WO 2008/116766 | 10/2008 |
| WO | WO 2008/128373 | 10/2008 |

OTHER PUBLICATIONS

European Search Report for EP Application No. 09009042, dated Jun. 1, 2010.
International Preliminary Report on Patentability for International App. No. PCT/EP2010/057456, dated Dec. 6, 2011.
International Search Report and Written Opinion for International App. No. PCT/EP2010/057456, completed Sep. 9, 2010.
Notification of Reasons for Refusal for Japanese Patent App. No. 2012-513559, dated Apr. 1, 2014.

\* cited by examiner

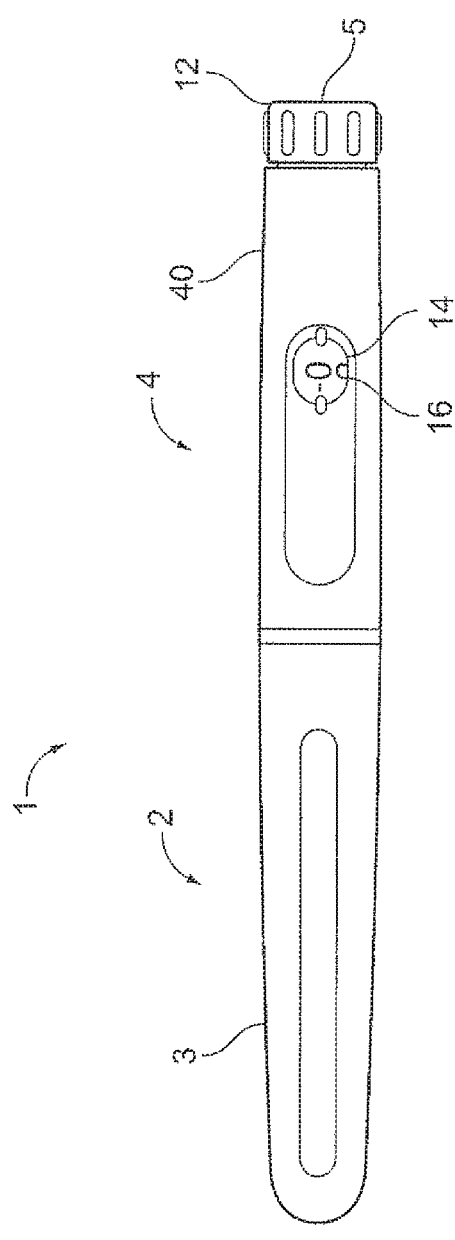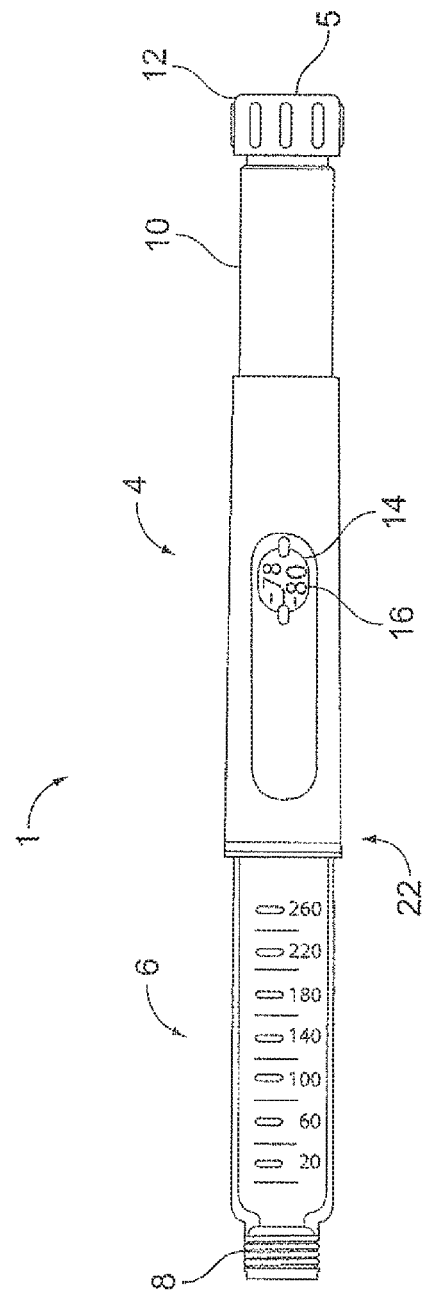

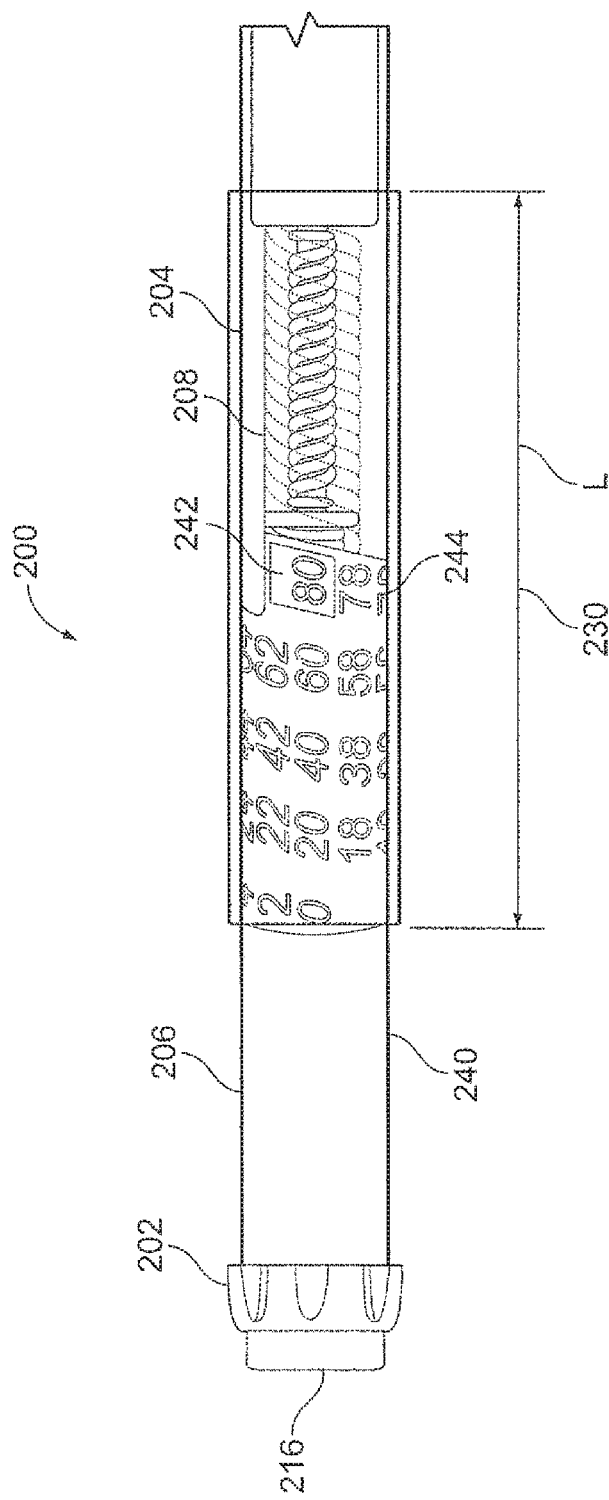

INNER HOUSING FOR A DRUG DELIVERY DEVICE

CROSS REFERENCE TO RELATED APPLICATIONS

The present application is a continuation of U.S. application Ser. No. 14/812,133, filed on Jul. 29, 2015, which is a continuation of U.S. application Ser. No. 13/375,186, filed on Mar. 9, 2012, which is a U.S. National Phase Application pursuant to 35 U.S.C. § 371 of International Application No. PCT/EP2010/057456, filed on May 28, 2010, which claims priority to U.S. Provisional Patent Application No. 61/182,818, filed on Jun. 1, 2009 and European patent Application No. 09009042.4, filed on Jul. 10, 2009. The entire disclosure contents of these applications are herewith incorporated by reference into the present application.

FIELD OF INVENTION

The present application is generally directed to dose setting mechanisms for drug delivery devices. More particularly, the present application is generally directed to a dose setting mechanism comprising an inner housing and used for drug delivery devices. Aspects of the invention may be equally applicable in other scenarios as well.

BACKGROUND

Pen type drug delivery devices have application where regular injection by persons without formal medical training occurs. This may be increasingly common among patients having diabetes where self-treatment enables such patients to conduct effective management of their disease.

There are basically two types of pen type delivery devices: resettable devices (i.e., reusable) and non-resettable (i.e., disposable). These types of pen delivery devices (so named because they often resemble an enlarged fountain pen) are generally comprised of three primary elements: (i) a cartridge section that includes a cartridge often contained within a housing or holder; (ii) a needle assembly connected to one end of the cartridge section; and (iii) a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then a dose is administered. Such removable needle assemblies may be threaded onto, or pushed (i.e., snapped) onto the pierceable seal end of the cartridge assembly.

The dosing section or dose setting mechanism is typically the portion of the pen device that is used to set a dose. During an injection, a spindle contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

Different types of pen delivery devices, including disposable (i.e., non-resettable) and reusable (i.e., resettable) varieties, have evolved over the years. For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism.

In contrast to typical disposable pen type devices, typical reusable pen delivery devices feature essentially two main reusable components: a cartridge holder and a dose setting mechanism. After a cartridge is inserted into the cartridge holder, this cartridge holder is attached to the dose setting mechanism. The user uses the dose setting mechanism to select a dose. Before the user injects the set dose, a replaceable double-ended needle assembly is attached to the cartridge housing.

This needle assembly may be threaded onto or pushed onto (i.e., snapped onto) a distal end of the cartridge housing. In this manner, a double ended needle mounted on the needle assembly penetrated through a pierceable seal at a distal end of the cartridge. After an injection, the needle assembly is removed and discarded. After the insulin in the cartridge has been exhausted, the user detaches the cartridge housing from the dose setting mechanism. The user can then remove the empty cartridge from the cartridge retainer and replace the empty cartridge with a new (filled) cartridge.

Aside from replacing the empty cartridge with a new cartridge, the user must somehow prepare the dose setting mechanism for a new cartridge: the dose setting mechanism must be reset to a starting or initial position. For example, in certain typical resettable devices, in order to reset the dose setting mechanism, the spindle that advances in a distal direction during dose injection must somehow be retracted back into the dose setting mechanism. Certain known methods of retracting this spindle back into the dose setting mechanism to a restart or an initial position are known in the art. As just one example, certain known reset mechanisms require a user to turn back or push back (retract) the spindle or some other portion of the dose setting mechanism.

Resetting of known dose setting mechanisms have certain perceived disadvantages. One perceived disadvantage is that the pen device user has to disassemble the device to either remove an empty cartridge or somehow reset the device. As such, another perceived disadvantage is that such devices have a high number of parts and therefore such devices are typically complicated from a manufacturing and from an assembly standpoint. For example, certain typical resettable pen type devices are not intuitive as to how a user must replace an empty cartridge or how a user is to reset the device. In addition, because such resettable devices use a large number of components parts, such resettable devices tend to be large and bulky, and therefore not easy to carry around or easy to conceal.

There is, therefore, a general need to take these disadvantages associated with resetting issues into consideration in the design and development of resettable drug delivery devices. Such desired drug delivery devices would tend to reduce the number of component parts and also tend to reduce manufacturing costs while also making the device less complex to assemble and manufacture. Such desired devices would also tend to simplify the steps required for a user to reset a dose setting mechanism while also making the device less complex and more compact in size.

SUMMARY

It is an object of the present invention to provide an improved dose setting mechanism for a drug delivery device.

This object is solved by a dose setting mechanism comprising an inner housing with means for guiding a dial sleeve and/or a driver of said mechanism.

According to an exemplary arrangement (first embodiment), a dose setting mechanism for a drug delivery device comprises an outer housing and an inner housing having an external groove. The inner housing guides the driver to dispense a dose set by the dose setting mechanism. A dial sleeve is disposed between the outer and inner housing and is rotatably engaged with the external groove of the inner housing. When a dose is set, the dial sleeve is rotated with respect to both the outer housing and the inner housing. The dial sleeve is translated away from both the outer housing and the inner housing. Preferably, said external groove of said inner housing comprises a helical groove having a constant pitch.

The inner housing may comprise an internal surface having a mechanical configuration that guides said driver to dispense said dose set by said dose setting mechanism. According to a first aspect of this embodiment, said mechanical configuration of said inner housing comprises a spline that guides said driver to dispense said dose set by said dose setting mechanism. Alternatively, said mechanical configuration of said inner housing may comprise a groove that guides said driver to dispense said dose set by said dose setting mechanism.

To improve the mechanical properties of the dose setting mechanism, said dial sleeve may have a generally smooth outer surface. Preferably, a scale arrangement is provided along a portion of said generally smooth outer surface. According to a further aspect of this embodiment, said scale arrangement provided along said portion of said generally smoother outer surface is viewable only through a window provided in an outer housing of said dose setting mechanism.

The dose setting mechanism may be coupled to a cartridge holder. For a disposable drug delivery device, said dose setting mechanism is permanently coupled to said cartridge holder.

In addition, the dose setting mechanism may further comprise a spindle which is operatively coupled to said driver, such that when said inner housing guides said driver to dispense said dose set by said dose setting mechanism, said driver pushes said spindle to act on a cartridge bung while said spindle translates in a distal direction to expel said dose from said cartridge.

Independent from the above mentioned features of the first exemplary arrangement (first embodiment), according to a second exemplary arrangement (second embodiment), a mechanism for setting a dose comprises a spindle for acting on a cartridge bung and a driver cooperating with the spindle. The arrangement also comprises an inner housing having an inner surface. The inner surface of the inner housing dictating movement of the driver during a dose dispensing step so that the spindle acts on the cartridge bung.

Preferably, said inner surface of said inner body comprises at least one longitudinal groove. As an alternative, said inner surface comprises at least a portion of a helical groove. As a further alternative, said inner surface may comprise a male groove guide.

Independent from the above mentioned features of the first and second exemplary arrangement, according to a third exemplary arrangement (third embodiment), a drug delivery device comprises an outer body and an inner body having an external helical groove. A dial sleeve is engaged with the external groove of the inner body and positioned between the outer body and the inner body. A driving member is positioned within the inner body. A clutch is operatively coupled to the dial sleeve and the driving member. The clutch allows the dial sleeve and the driving member to rotate together during a setting of a dose of the drug delivery device.

In addition, a spindle may be provided operatively coupled to said driving member, such during said injection of said dose, said inner body guides said driving member and said driving member driver pushes said spindle to dispel a dose of medication from a cartridge. Further, said spindle may comprise at least one groove, said at least one groove allowing said spindle to translate in a distal direction to expel said dose from said cartridge.

Independent from the above mentioned features of the first, second and third exemplary arrangement, according to a fourth exemplary arrangement (fourth embodiment), a dose setting mechanism for a drug delivery device is provided comprising an outer housing, an inner housing, a driver and a dial sleeve. The inner housing has an external groove, with said inner housing being operatively coupled to the driver and guiding said driver to dispense a dose set by said dose setting mechanism. The dial sleeve is disposed between said outer housing and said inner housing, with the dial sleeve being rotatably engaged with said external groove of said inner housing, such that when a dose is set by said dose setting mechanism, said dial sleeve and driver are both rotated with respect to both said outer housing and said inner housing and are translated away from both said outer housing and said inner housing. Preferably, the external groove of said inner housing comprises a helical groove having a constant pitch.

According to a further development of this fourth embodiment, the inner housing comprises an internal surface, which comprises a mechanical configuration that guides said driver to dispense said dose set by said dose setting mechanism. The mechanical configuration of said inner housing may comprise a spline that guides said driver to dispense said dose set by said dose setting mechanism. As an alternative, the mechanical configuration of said inner housing may comprise a groove that guides said driver to dispense said dose set by said dose setting mechanism.

To improve the mechanical properties of the dose setting mechanism, said dial sleeve may have a generally smooth outer surface. Preferably, a scale arrangement is provided along a portion of said generally smooth outer surface. According to a further aspect of this embodiment, said scale arrangement provided along said portion of said generally smoother outer surface is viewable only through a window provided in an outer housing of said dose setting mechanism.

The dose setting mechanism may be coupled to a cartridge holder. For a disposable drug delivery device, said dose setting mechanism is permanently coupled to said cartridge holder.

According to a further aspect of this fourth embodiment a spindle is provided, which is operatively coupled to said driver, such that when said inner housing guides said driver to dispense said dose set by said dose setting mechanism, said driver pushes said spindle to act on a cartridge bung while said spindle translates in a distal direction to expel said dose from said cartridge.

A further aspect of the present invention is directed to the ratio of the length of the inner housing or body to the length of further components of the dose setting mechanism of a drug delivery device. Preferably, the inner housing has a length L in its axial direction which is essentially the same as the length of the dose setting mechanism, or the outer housing or the dose dial sleeve. Although it is preferred to choose the length L of the inner housing being nearly exactly the same as the length of the outer housing, preferred embodiments include a length L of the inner housing being between about 75% to about 125%, preferably between 90% and 110%, of the length of the dose setting mechanism, or the outer housing or the dose dial sleeve.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 1 illustrates a first embodiment of a resettable drug delivery device;

FIG. 2 illustrates the drug delivery device illustrated in FIG. 1 with the cap removed;

FIG. 13 illustrates the dose setting mechanism illustrated in FIG. 12 in which a user has set a dose.

DETAILED DESCRIPTION

Figure 3:
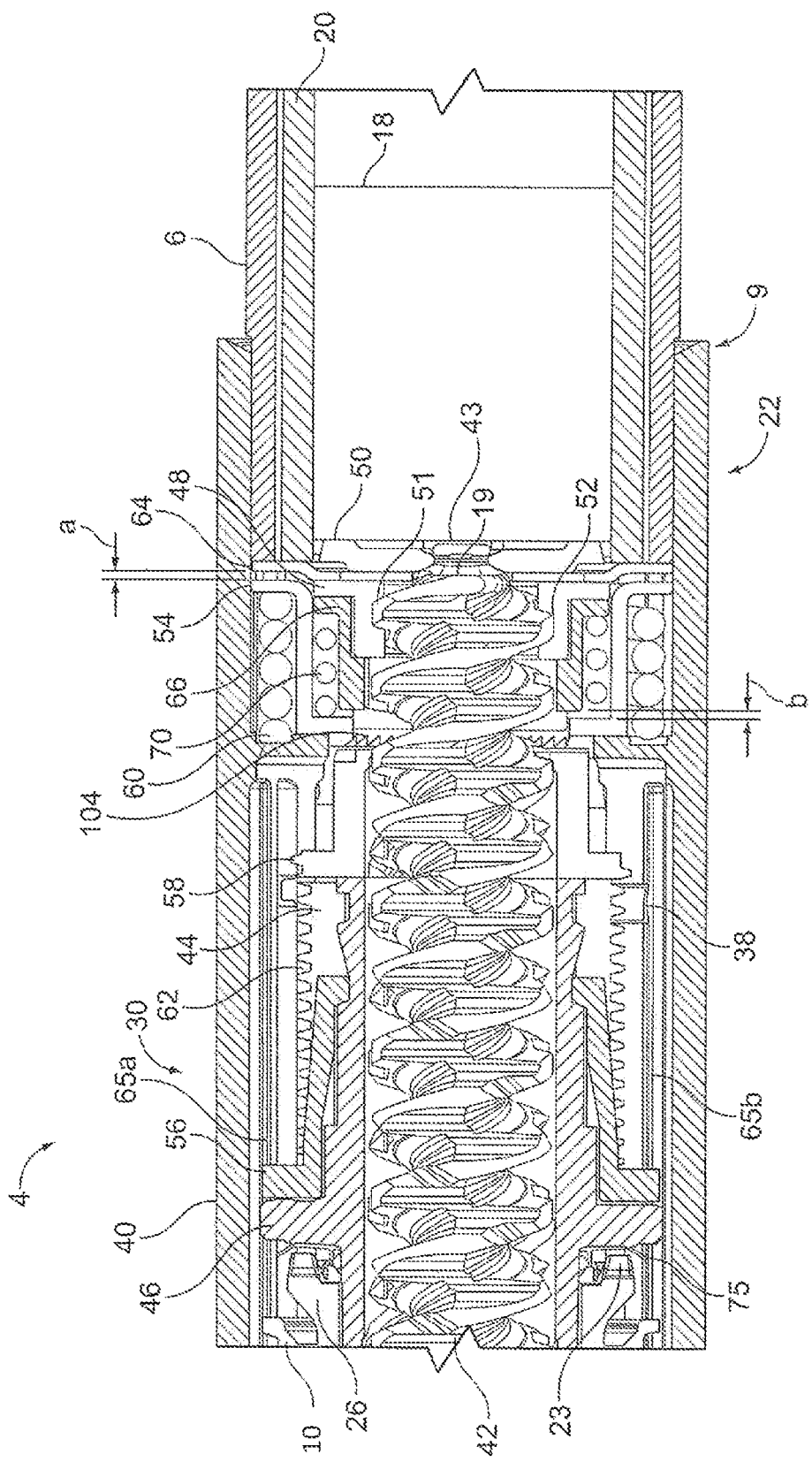
FIG. 3 illustrates a sectional view of the first embodiment of the drug delivery device of FIG. 2 in a first position.

Referring to FIG. 1, there is shown a drug delivery device 1 in accordance with a first arrangement of the present invention. The drug delivery device 1 comprises a housing having a first cartridge retaining part 2, and dose setting mechanism 4. A first end of the cartridge retaining part 2 and a second end of the dose setting mechanism 4 are secured together by retaining features. In this illustrated arrangement, the cartridge retaining part 2 is secured within the second end of the dose setting mechanism 4. A removable cap 3 is releasably retained over a second end or distal end of a cartridge retaining part. As will be described in greater detail, the dose setting mechanism 4 comprises a dose dial grip 12 and a window or lens 14. To set a dose of medication contained within the drug delivery device 1, a user rotates the dose dial grip 12 and the window allows a user to view the dialed dose by way of a dose scale arrangement 16.

FIG. 2 illustrates the medical delivery device 1 of FIG. 1 with the cover 3 removed from the distal end of the medical delivery device. As illustrated, a cartridge 20 from which a number of doses of a medicinal product may be dispensed is provided in the cartridge housing 6. Preferably, the cartridge 20 contains a type of medicament that is administered often, such as once or more times a day.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

A bung or stopper (not illustrated in FIG. 2) is retained in a first end or a proximal end of the cartridge 20.

The dose setting mechanism 4 of the drug delivery device illustrated in FIG. 2 may be utilized as a reusable (and hence resettable) or a non-reusable (and hence non-resettable) drug delivery device. Where the drug delivery device 1 comprises a reusable drug delivery device, the cartridge is removable from the cartridge housing 6. The cartridge 20 may be removed from the device without destroying the device by merely the user disconnecting the dose setting mechanism 4 from the cartridge holder 6.

In use, once the removable cap 3 is removed, a user can attach a suitable needle assembly to the distal end of the cartridge holder. Such needle unit may be screwed onto a distal end of the housing or alternatively may be snapped onto this distal end. A replaceable cap 3 is used to cover the cartridge holder 6 extending from the dose setting mechanism 4. Preferably, the outer dimensions of the replaceable cap 3 are similar or identical to the outer dimensions of the dose setting mechanism 4 so as to provide an impression of a unitary whole when the replaceable cap 3 is in position covering the cartridge holder 2.

FIG. 3 illustrates a sectional view of the dose setting mechanism 4 removably connected to the cartridge holder 6. The dose setting mechanism 4 comprises an outer housing 40 containing a spindle 42, a number sleeve 10, a clicker 75, a clutch 26, and a driver 30. A first helical groove 19 extends from a first end of a spindle 42. In one arrangement, the spindle 42 is generally circular in cross section however other arrangements may also be used. The first end of the spindle 42 (a distal end 43 of the spindle 42) extends through a pressure plate 64. A spindle bearing 50 is located at the distal end 43 of the spindle 42. The spindle bearing 50 is disposed to abut a second end of the cartridge piston 18. The driver 30 extends about the spindle 42.

The clutch 26 is disposed about the driver 30, between the driver 30 and a number sleeve 10. The clutch 26 is located adjacent the second end of the driver 30. A number sleeve 10 is provided outside of the clutch 26 and radially inward of the housing 40. The main housing 40 is provided with a window 14 through which a part of an outer surface 11 of the number sleeve 10 may be viewed.

Returning to FIGS. 1-2, a dose dial grip 12 is disposed about an outer surface of the second end of the number sleeve 10. An outer diameter of the dose dial grip 12 preferably corresponds to the outer diameter of the housing 40. The dose dial grip 12 is secured to the number sleeve 10 so as to prevent relative movement between these two components. In one preferred arrangement, the dose dial grip 12 and number sleeve 10 comprise a one piece component that is rotationally coupled to a clutch and drive sleeve and axially coupled to the number sleeve 10. However, alternative coupling arrangements may also be used.

Returning to FIGS. 3-5, in this arrangement, driver 30 comprises a first driver portion 44 and a second driver portion 46 and these portions extend about the spindle 42. Both the first and the second driver portions 44, 46 are generally cylindrical. As can be seen from FIG. 6, the first drive portion 44 is provided at a first end with a first radially extending flange 56. A second radially extending flange 58 is provided spaced a distance along the first driver portion 44 from the first flange 56. An intermediate helical groove 62 is provided on an outer part of the first driver portion 44 extending between the first flange 56 and the second flange 58. A portion or a part helical groove 68 extends along an internal surface of the first driver portion 44. The spindle 42 is adapted to work within this part helical groove 68.

A dose limiter 38 (illustrated in FIG. 3) is located between the driver 30 and the housing 4, disposed between the first flange 56 and the second flange 58. In the illustrated arrangement, the dose limiter 38 comprises a nut. The dose limiter 38 has an internal helical groove matching the helical groove 62 of the driver 30. In one preferred arrangement, the outer surface of the dose limiter 38 and an internal surface of the housing 40 are keyed together by way of splines. This prevents relative rotation between the dose limiter 38 and the housing 40 while allowing relative longitudinal movement between these two components.

Referring back to FIGS. 2-5, essentially, in normal use, the operation of the dose setting mechanism 4 occurs as follows. To dial a dose in the arrangement illustrated in FIGS. 1-5, a user rotates the dose dial grip 12. The driver 30, the clutch 26 and the number sleeve 10 rotate along with the dose dial grip 12. In this preferred arrangement, the clicker 75 is disposed between a distal end 23 of the clutch 26 and a flange 80 of the drive sleeve 46. The clicker 75 and the internal surface of the housing 40 are keyed together by way of splines 65a, 65b. This prevents rotation of the clicker 75 with respect to the housing 40 either during dose selection or during dose administration.

The number sleeve 10 extends in a proximal direction away from the housing 40. In this manner, the driver 30 climbs the spindle 42. As the driver 30 and the clutch rotates, a distal portion 23 of the clutch drags over the clicker 75 to produce a click. Preferably, the distal portion includes a plurality of splines that are disposed such that each click corresponds to a conventional unit dose, or the like.

At the limit of travel, a radial stop on the number sleeve 10 engages either a first stop or a second stop provided on the housing 40 to prevent further movement. Rotation of the spindle 42 is prevented due to the opposing directions of the overhauled and driven threads on the spindle 42. The dose limiter 38, keyed to the housing 40, is advanced along the thread 62 by the rotation of the driver 30.

FIG. 2 illustrates the medical delivery device after a desired dose of 79 International Units (IU) has been dialed. When this desired dose has been dialed, the user may then dispense the desired dose of 79 IU by depressing the dial grip. As the user depresses the dial grip 12, this displaces the clutch 26 axially with respect to the number sleeve 10, causing the clutch 26 to disengage. However the clutch 26 remains keyed in rotation to the driver 30.

The driver 30 is prevented from rotating with respect to the main housing 40 but it is free to move axially with respect thereto. The longitudinal axial movement of the driver 30 causes the spindle 42 to rotate and thereby to advance the piston 18 in the cartridge 20.

In normal use, the first and second portions 44, 46 of the driver 30 are coupled together when the dose dial sleeve 10 is rotated. That is, in normal use, the first and second portions 44, 46 of the driver 30 are coupled together with the dose dial sleeve 10 when a user sets a dose by turning the dose dial grip 12. After each dispensed dose, the spindle 42 is pushed in a distal direction, acting on the bung 18 of the cartridge 20 to continue to expel a dialed dose of medication out of an attached needle assembly releasably connected to the distal end 8 of the cartridge holder 6.

After a user uses the drug delivery device 1 to dispense all of the medication contained in the cartridge 20, the user may wish to replace the empty cartridge in the cartridge holder 6 with a new cartridge. The user must then also reset the dose setting mechanism 4: for example, the user must then retract or push the spindle 42 back into the dose setting mechanism 4.

If the user decides to replace an empty cartridge and reset the device 1, the first and second driver portions 44, 46 must be de-coupled from one another. After decoupling the first driver portion 44 from the second driver portion 46, the first driver portion 44 will be free to rotate while the second driver portion 46 will not be free to rotate.

Figure 7:
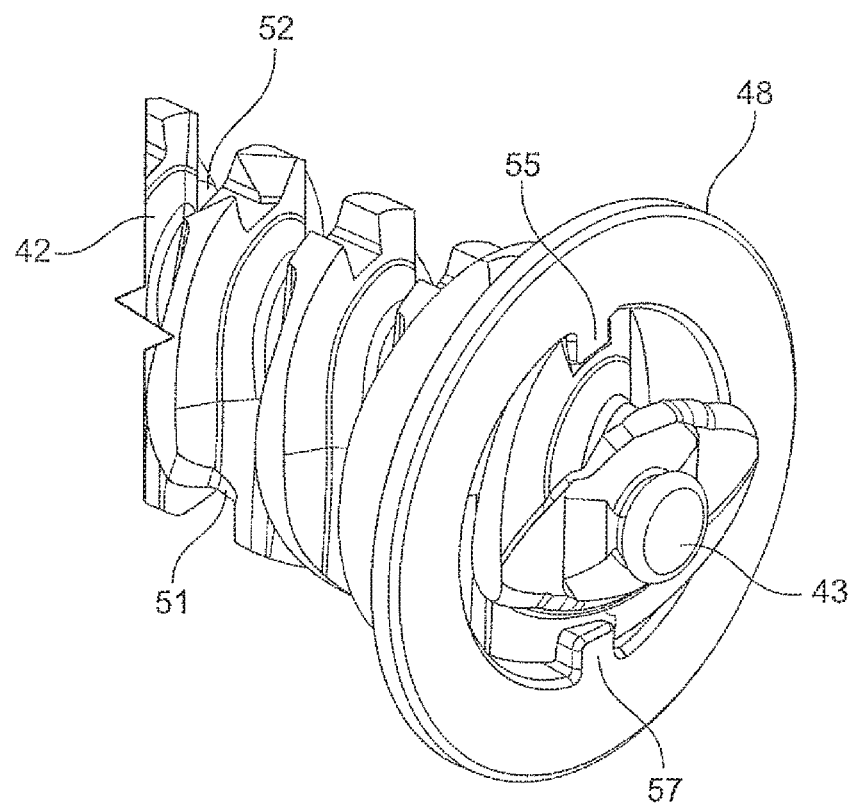
FIG. 7 illustrates a distal end of the spindle of the dose setting mechanism illustrated in FIGS. 2-5.

During a device resetting step, rotating the first driver portion 44 achieves at least two results. First, rotation of the first driver portion 44 will reset the axial position of the spindle 42 with respect to the dose setting mechanism 4 since rotation of the first driver portion 44 causes the spindle 42 to rotate. Rotation of the spindle 42 (because the spindle is splined with the spindle guide 48) moves the spindle in a proximal direction back into the dose setting mechanism. For example, FIG. 7 illustrates one arrangement for connecting the spindle 42 to the spindle guide 48. In FIG. 7, the spindle 42 comprises a first spline 51 and a second spline 52. The spindle guide 48 comprises an essentially circular member having an aperture. The aperture includes two inner protruding members 55, 57 that engage the first and second splines 51, 52 respectively, so that the spindle guide 48 locks onto the spindle and rotates along with the spindle during spindle rotation.

Second, rotation of the first driver portion 44 will also axial move or reset a dose limiter 38 to an initial or start position. That is, as the first driver portion 44 is rotated back to an initial start position, because the dose limiter 38 is threadedly engaged to the outer groove and splined to an inner surface of a housing portion, such as the outer housing 40. In this configuration, the dose limiter 38 is prevented from rotating but will move along the outer groove 62 of the first driver portion 44 as this portion is rotated during a resetting step. In addition, because it is splined to longitudinal splines 65*a*, 65*b* of the outer housing 4, the clicker 75 is also prevented from rotating during this resetting step.

Referring to a first driver arrangement illustrated in FIG. 3, the two portions of the driver 30 are decoupled when the first driver portion 44 is pulled axially away from the second driver portion 46. This may be achieved by the use of a biasing means (such as at least one spring) that interacts together when the cartridge holder 6 is removed from the front or distal end of the device to first lock the relative rotation between the spindle 42 and a spindle guide 48 through which the spindle passes, and then to push this spindle guide 48 and also nut 66 axially a fixed distance. Because the spindle 42 is rotationally locked to this spindle guide 48 and is threadedly engaged with the spindle nut 66, the spindle 42 will move axially.

The spindle 42 is coupled via a groove engaged to the first driver portion 44. The first driver portion 44 is prevented from rotation by a clutched connection to the second driver portion 46. In one preferred arrangement, the second driver portion 46 is prevented from rotation by the clicker detent 75 which resides between the clutch and the flange 80 of the drive sleeve 46. Therefore, axial movement of the spindle 42 decouples the two driver portions 44, 46 so that the clutched connection becomes de-coupled.

Figure 4:
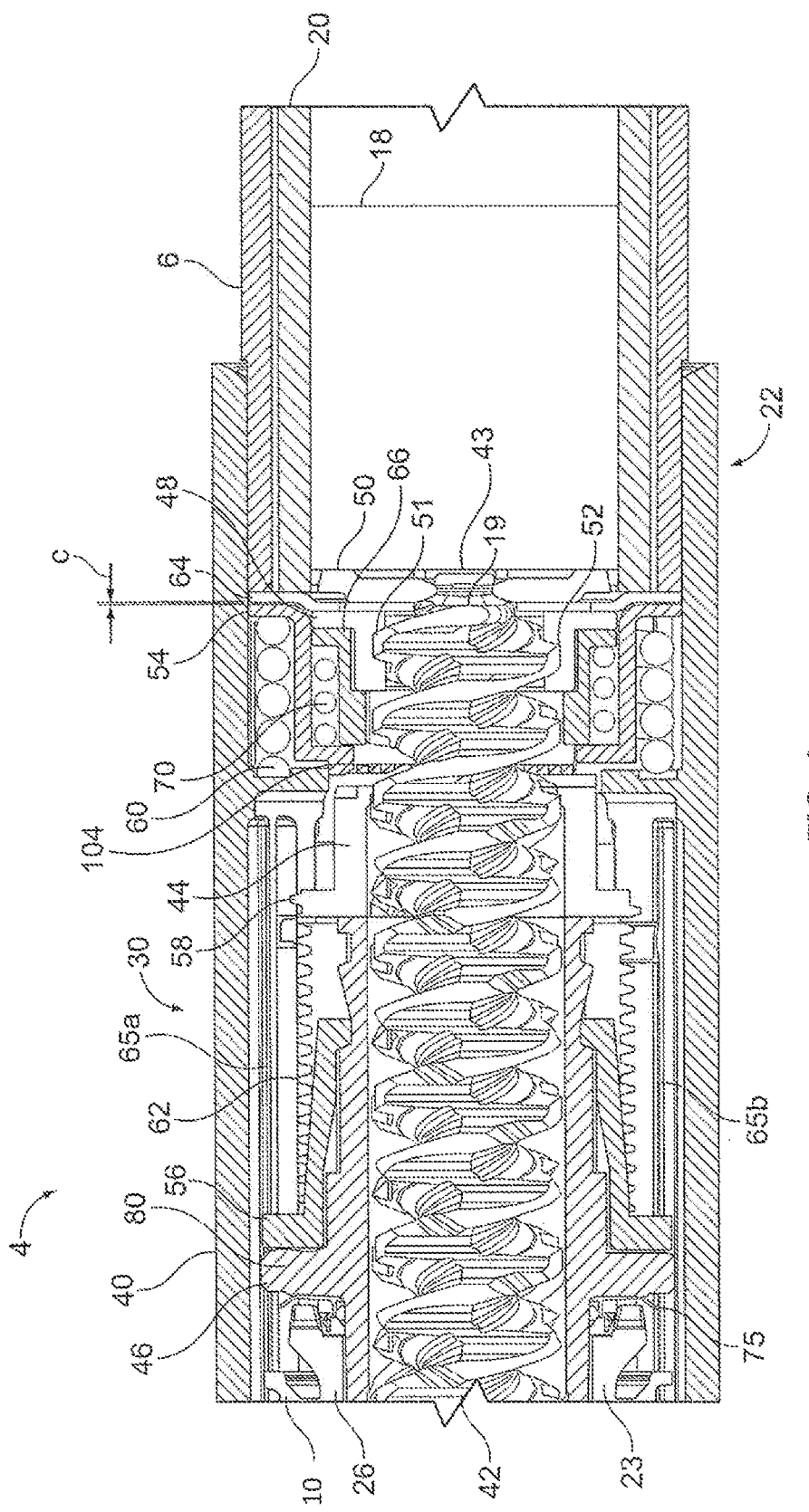
FIG. 4 illustrates a sectional view of the first embodiment of the drug delivery device of FIG. 2 in a second position.
Figure 5:
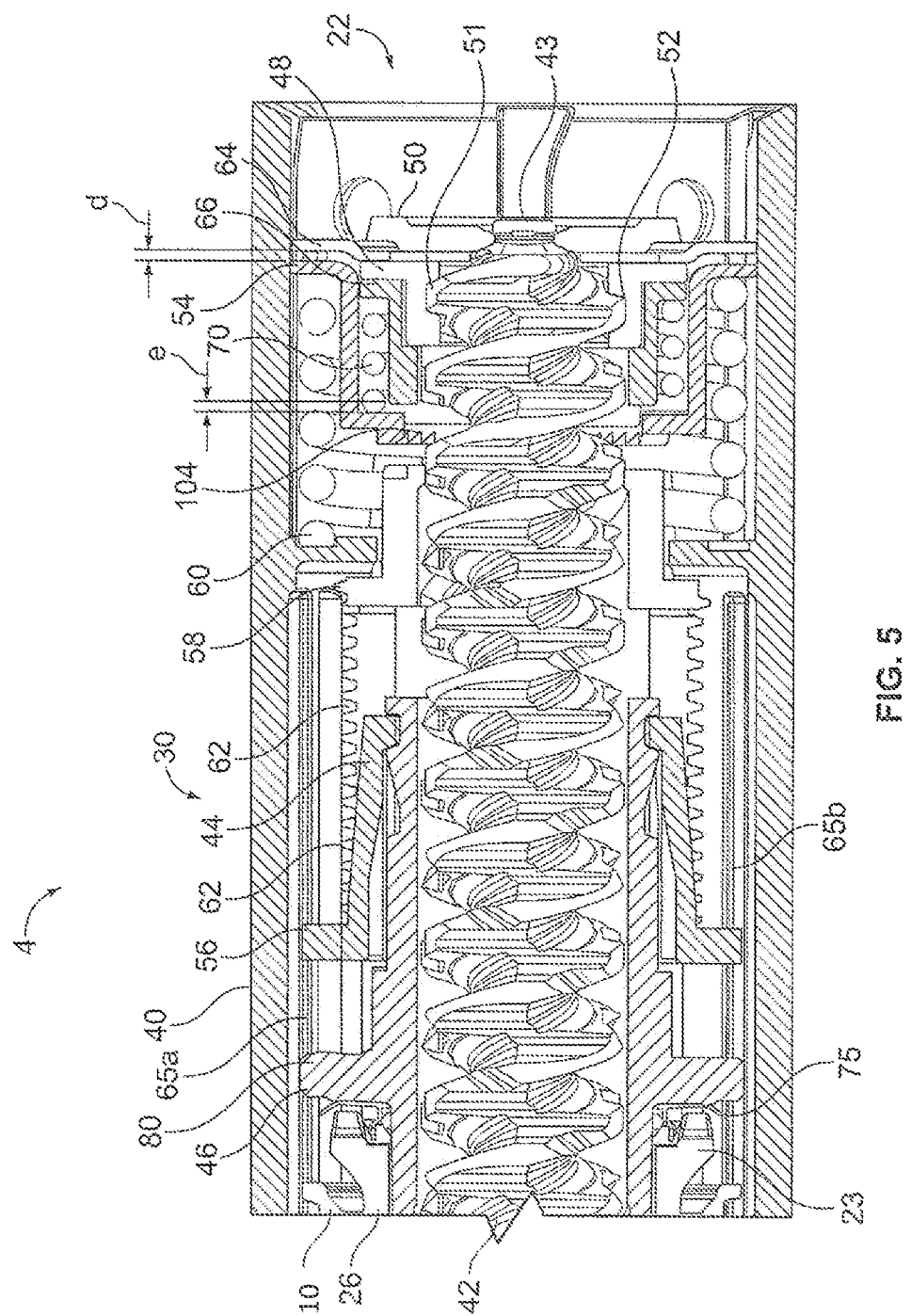
FIG. 5 illustrates a sectional view of the first embodiment of the drug delivery device of FIG. 2 in a third position.

This sequence of operation as the cartridge holder 6 is removed or disconnected from the dose setting mechanism 4 is illustrated in FIGS. 3-5. In FIG. 3, the various component parts of the drug delivery device include: a dose setting housing 40, a cartridge 20, a spindle 42, first driver portion 44; second driver portion 46, spindle bearing 50, spindle guide 48 a spring plate 54; a main spring 60, a pressure plate 64, a cartridge holder 20; a spindle nut 66; and a second spring 70. In this preferred arrangement, the spindle guide 48 is rotationally fixed relative to the spindle 20. In addition, the spring plate 54 pressure plate 64 and spindle nut 66 are all rotationally fixed relative to the outer housing.

In FIG. 3, the cartridge holder 6 is fitted via apertures in the pressure plate 64 and applies a load to the spring plate 54. This compresses the first biasing means or main spring 60. These apertures in the pressure plate 64 (not shown) allow the pressure plate 64 to move away from the spring plate 54 (in a distal direction towards the cartridge holder 6) under the action of the second biasing means or second spring 70. This will open up a Gap "a" as shown in FIG. 3. Gap "a" is a gap created between the pressure plate 64 and the spring plate 54. This will also open Gap "b", a gap between the spindle nut 66 and the spring plate 54. This Gap b is illustrated in FIG. 3. The Gap b in conjunction with the light force from the second spring or biasing means 70 moves the spindle nut 66 towards the distal end of the drug delivery device 1. This applies light pressure to the spindle guide 48.

The spindle guide 48 is compressed under the action of the second spring 70 between the spindle nut 66 and pressure plate 64. This light force coupled with the friction coefficient on either side of a flange of the spindle guide 48 through which this force acts, provides a resistance to rotation of the spindle guide 48 and therefore a resistance to rotation of spindle 42 as well. One advantage of this configuration is that at the end of a dose, it is advantageous to prevent the spindle 42 from back-winding into the dose setting mechanism 4 under light residual loads that may remain from the cartridge bung 18. By preventing the spindle 42 from back-winding in a proximal direction, a distal end 43 of the spindle 42 (and hence the spindle bearing 50) remains on the bung 18. Maintaining the distal end 43 of the spindle 42 on the bung 18 helps to prevent a user from administrating a potential under-dose.

When the user delivers a dose, as the dispense force increases, the rearward load on the spindle nut 66 increases to a point at which the spindle nut 66 travels back in a proximal direction and compresses the second spring 70. This releases the axial force acting on the spindle guide 48. This removes the resistance to rotation of the spindle guide 48 and hence spindle 42. This configuration therefore prevents back-winding of the spindle 42 under low loads caused by the cartridge bung 18 but does not add to the dispense force once this dispense force has increased above a certain threshold level.

FIG. 4 illustrates the dose setting mechanism 4 of FIG. 3 with the cartridge holder 6 rotated to release a connection type between the housing 40 of dose setting mechanism 4 and the cartridge holder 6. In one arrangement, this connection type 22 is a bayonet connection. However, those of ordinary skill in the art will recognize that other connection types 22 may be used as well such as threads, snap locks, snap fits, luer locks and other similar connection types. In the arrangement illustrated in FIGS. 3-5, by rotating the cartridge holder 6 with respect to housing 40, features that were initially acting on the spring plate 54 to compress the main biasing means 60 through apertures in the pressure plate 64, rotate so that they now release this force created by the main biasing means 60. This allows the spring plate 54 to move in a distal direction until the spring plate 54 contacts the spindle nut 66 on an inside face of the spindle nut 66.

In this second condition, the previous discussed Gap "a" (from FIG. 3) has now been reduced to a Gap "c" (as seen in FIG. 4). In this manner, the relative high axial force from the main biasing means 60 acts through the spring plate 54 to the spindle nut 66 and from the spindle nut 66 through the spindle guide 48 to the pressure plate 64. This relative high axial force from the main biasing means 60 is sufficient to prevent the spindle guide 48, and hence spindle 42, from rotating.

After sufficient rotation of the cartridge holder 6, the cartridge holder 6 disengages from the connection type 22 with the housing 40. The cartridge holder 6 is then driven in an axial direction away from the housing 40 by the main biasing means 60 (i.e., in a distal direction). However, during this movement, the main spring 60 continues to load the cartridge holder 6 through the spindle guide 48 and therefore the spindle 42 is prevented from rotation. As the spindle 42 is also threaded to the first driver portion 44, the first driver portion 44 is also pulled axially in a distal direction and in this manner becomes disengaged from the second driver portion 46. The second driver portion 46 is axially fixed and is prevented from rotation. In one arrangement, the second driver portion 46 is prevented from rotation by clicker elements and prevented from axial movement by its axial coupling to the number sleeve.

FIG. 5 illustrates the dose setting mechanism illustrated in FIG. 3 in a third position, that is, with the cartridge holder 6 removed. As the cartridge holder 6 is removed from the housing 40, the bayonet features shown in FIG. 5 (illustrated as round pegs extending radially inwards on inside of inner housing), limit travel of the pressure plate 64 but allows Gap "c" (as shown in FIG. 4) to increase to a wider Gap "d" (as shown in FIG. 5). As a result, Gap "e" develops. Gap "e" removes the high spring force created by the main biasing means 60 from the spindle guide 48. The dose setting mechanism 4 in FIG. 4 is now ready to be reset.

To reset this dose setting mechanism 4, a user retracts the spindle 42 in a proximal direction back into the housing 40 by pushing on the distal end 43 of the spindle 42. Therefore, during this re-setting step of the dose setting mechanism 4, as the spindle 42 is pushed back into the dose setting mechanism 4, the movement of the spindle 42 causes the spindle nut 66 to move back against a light spring force created by the second biasing means 70. This movement releases the axial load and hence resistance to rotation from the spindle guide 48. Therefore, as the dose setting mechanism 4 is reset by the spindle 42 rotating back into the dose setting mechanism 4, the spindle guide 48 also rotates.

As the spindle 42 is pushed back further into the dose setting mechanism 4, the spindle 42 rotates through the spindle nut 66. As the first driver portion 44 is de-coupled from the second driver portion 46, the first driver portion 44 rotates (with the flexible elements 102, 103 running on a conical surface groove 90 formed by the first annular ring 91 on the second half of the drive sleeve 46, FIGS. 5 and 6). This accommodates the axial and rotational movement of the spindle 42.

As the first driver portion 44 rotates during reset, first driver portion 44 also re-sets the dose nut. More specifically, as the first driver portion 44 rotates, the dose nut which is not rotatable since it is splined to an inner surface of the housing 40, traverses along the helical groove 62 provided along an outer surface of the first driver portion 44 and traverses back to an initial or starting position. In one preferred arrangement, this starting position of the dose nut resides along the first radial 56 flange of the first driver portion 44.

After the dose setting mechanism 4 has been reset, the dose setting mechanism 4 must be re-connected to the cartridge holder 6. When re-connecting these two components, the process generally works in reverse. However, this time the axial compression of the main spring 60 causes the first driver portion 44 to re-engage with the second driver portion 46. In this manner, the flexible elements re-engage with the second annular ring 94 on the second driver portion 46.

Figure 6:
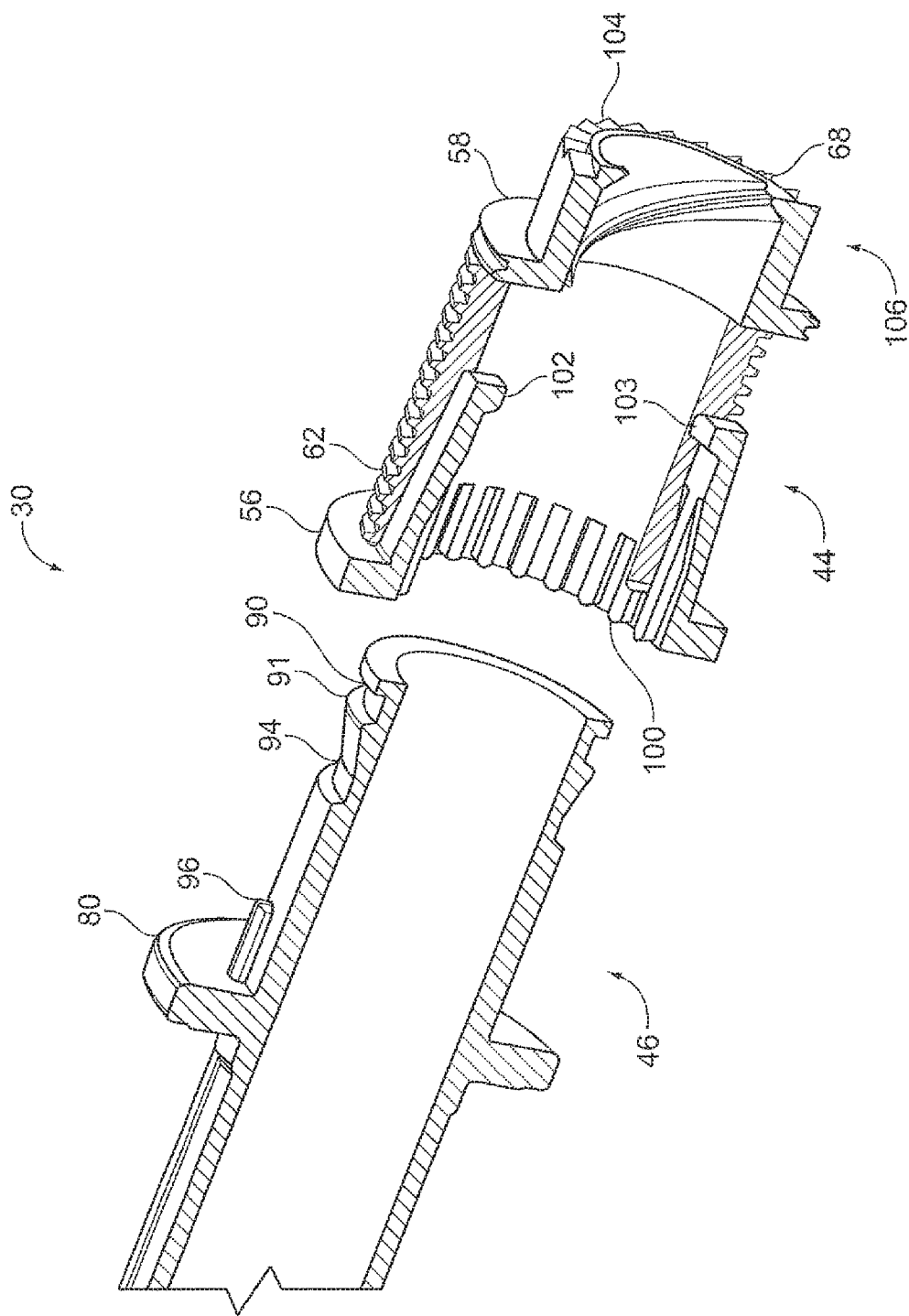
FIG. 6 illustrates a first arrangement of the driver illustrated in FIGS. 2-5 comprising a first driver portion and a second driver portion.

FIG. 6 illustrates a first arrangement of the second driver portion 46 and the first driver portion 44 illustrated in FIGS. 3. As shown in FIG. 6, second driver portion 46 is generally tubular in shape and comprises a first annular groove 90 at a distal end of the second driver portion 46. The first annular groove 90 comprises a conical face 91. The second driver portion further comprises a second annular groove 94 and at least one spline 96 positioned along a surface of the second driver portion.

The first driver portion 44 is also generally tubular in shape and comprises a first and a second flexible element 102, 103 and a plurality of spline recesses 100. These plurality of recesses 100 releasably connect the longitudinal spline 96 of the first driver portion 44 to second driver portion 46 when both first and second driver portions 44, 46 are pushed axially together so that they releasably engage one another. When pushed together, the flexible elements 102, 103 of the first driver portion 44 are pushed over the first annular groove 90 of the second driver portion 46 and then stop when the flange 80 of the second driver portion abuts the first axial flange 56 of the first driver portion 44.

The first driver portion 44 also includes a plurality of ratchet features 104. These ratchet features 104 are provided at a distal end 106 of the first driver portion 44. These ratchet features 104 engage similar ratchet features on the spring plate 25 which are splined to the housing 2. (See e.g., FIGS. 3-5) At the end of the re-setting step, these ratchet features engage one another so as to prevent the first driver portion 44 from rotating. This ensures that as the spindle 42 is reset further, the first driver portion moves axially to re-engage the second driver portion 46 rather than rotate on the conical face 90. These features also orientate the spring plate 25 relative to the second driver portion 44 so that the two driver portions 44, 46 engage easily during assembly or after reset. Therefore, these ratchet features also prevent the coupling features 100, 96 from clashing with one another.

Figure 8:
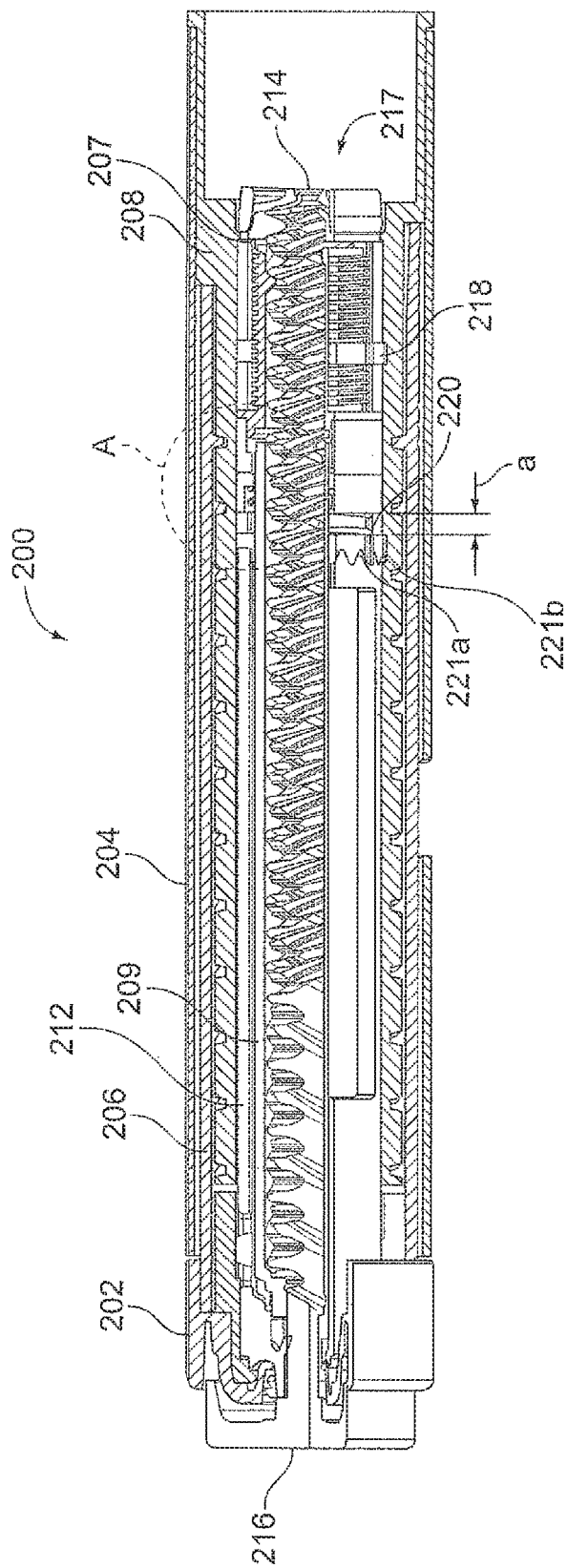
FIG. 8 illustrates a sectional view of a second embodiment of a dose setting mechanism of the drug delivery device illustrated in FIG. 1.
Figure 9:
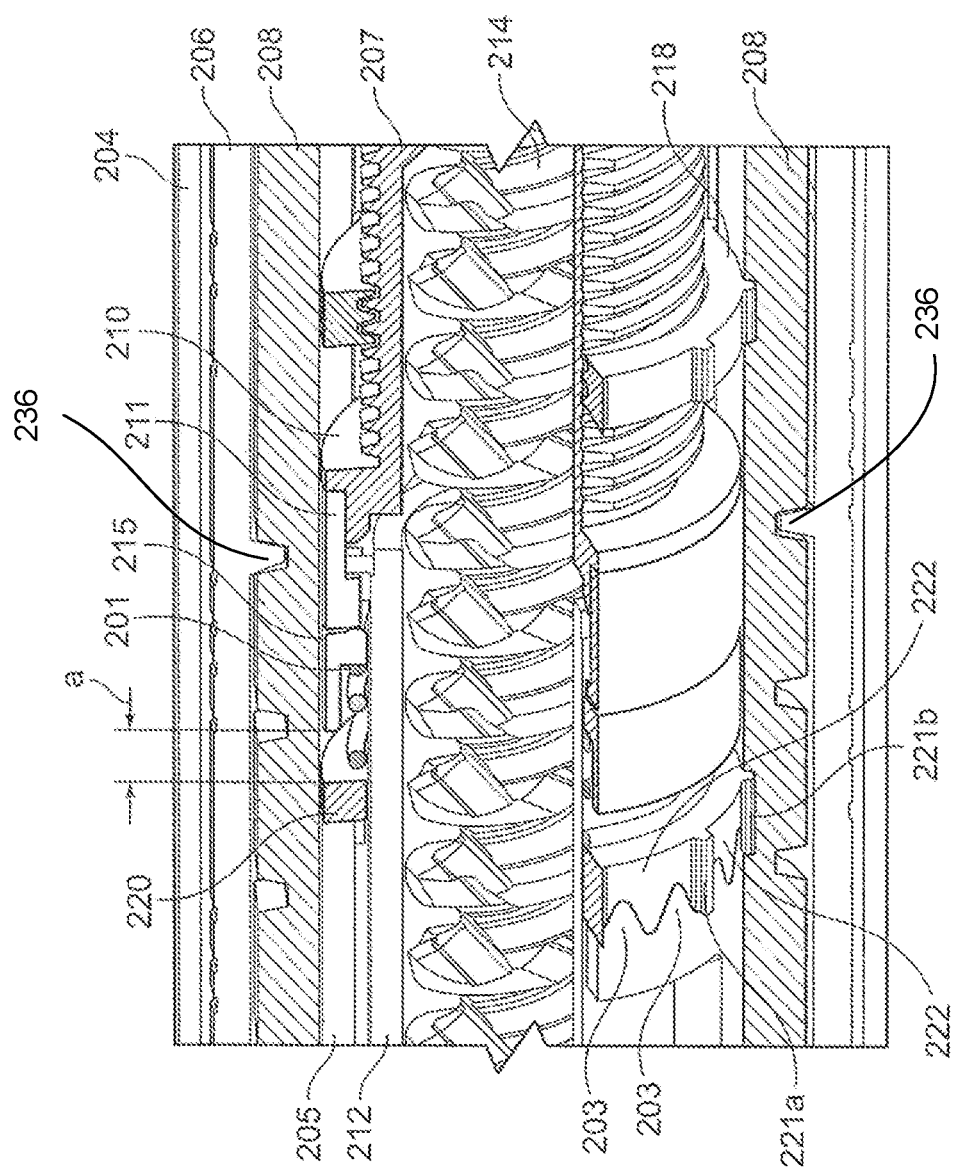
FIG. 9 illustrates a partial sectional view of the second embodiment of the dose setting mechanism illustrated in FIG. 8.
Figure 10:
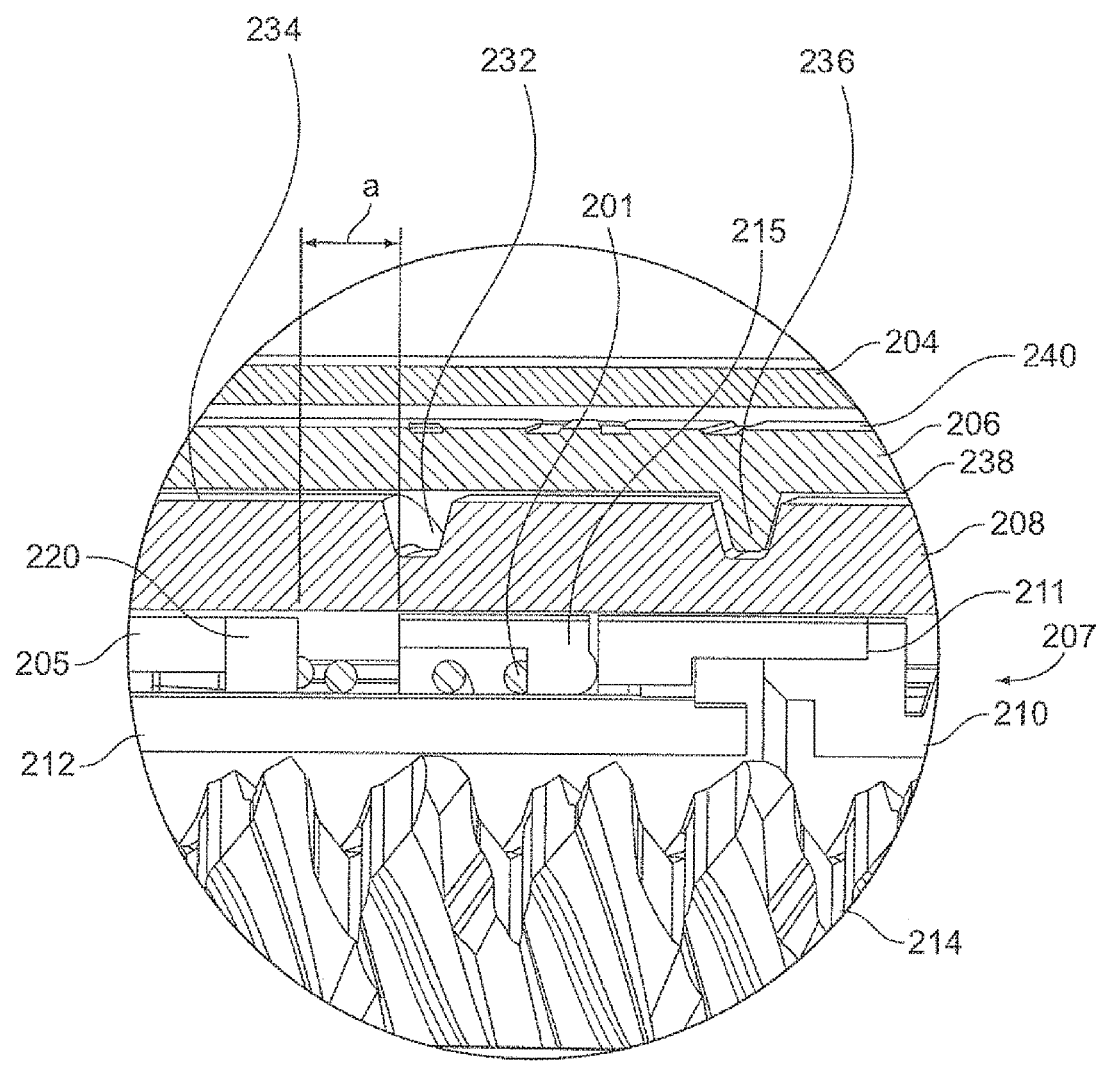
FIG. 10 illustrates a close up view of Gap a illustrated in FIG. 8.

A second arrangement of resettable dose setting mechanism is illustrated in FIGS. 8-10. FIG. 8 illustrates a section view of a second arrangement of a dose setting mechanism 200. Those of skill in the art will recognize that dose setting mechanism 200 may include a connection mechanism for releasably connecting to a cartridge holder, like the cartridge holder 6 illustrated in FIG. 2. However, as those of ordinary skill in the art will recognize, the dose setting mechanism may also include a permanent connection mechanism for permanently connecting to a cartridge holder.

FIG. 9 illustrates a portion of the dose setting mechanism illustrating the driver operation. FIG. 10 illustrates a close up view of the coupling between the first driver portion and the second driver portion illustrated in FIG. 9. The second arrangement of the dose setting mechanism 200 operates in generally a similar fashion to the first arrangement of the dose setting mechanism 4 illustrated in FIGS. 1-5.

With reference to FIGS. 8-10, the dose setting mechanism 200 comprises a dose dial grip 202, a spring 201, an outer housing 204, a clutch 205, a driver 209, a number sleeve 206, a clicker 220 and an inner housing 208. Similar to the driver 30 illustrated in FIGS. 2-5, driver 209 of dose setting mechanism comprises a first driver portion 207 and a second driver portion 212. In one arrangement, the first driver portion 207 comprises a first component part 210 and a second component part 211. Alternatively, the first driver portion 207 is an integral component part.

Where the dose setting mechanism 200 illustrated in FIGS. 8 and 9 comprises a resettable dose setting mechanism, the driver 209 is de-coupled from the dose setting mechanism 200 when the first driver portion 207 is pushed axially towards the second driver portion 212 (i.e., pushed in a proximal direction). In one arrangement, this may be achieved by pushing axially on a distal end of the spindle 214. This does not require any mechanism associated with removal of a cartridge holder. The mechanism is also designed such that the first and second driver portions 207, 212 and the spindle 214 remain locked together rotationally during dose setting as well as during dose administration.

An axial force on the spindle 214 causes the spindle 214 to rotate due to its threaded connection to the inner housing 208. This rotation and axial movement of the spindle 214 in turn causes the first driver portion 207 to move axially towards the second driver portion 212. This will eventually de-couple the coupling elements 250 between the first driver portion 207 and second driver portion 212. This can be seen from FIG. 11.

This axial movement of the first driver portion 207 towards the second driver portion 212 results in certain advantages. For example, one advantage is that the metal spring 201 will compress and will therefore close the Gap a illustrated in FIGS. 8-10. This in turn prevents the clutch 205 from disengaging from the clicker 220 or from the number sleeve 206. As illustrated in FIG. 9, a distal end of the clutch 205 comprise a plurality of clutch teeth 203. These clutch teeth 203 engage a plurality of clicker teeth 222 disposed at a proximal end of the clicker 220. As such, when a user dials a dose, these clutch and clicker teeth engage one another to produce a click. Preferably, the clicker teeth 222 are disposed such that each click corresponds to a conventional unit dose, or the like. Therefore, when the dose dial grip 202 and hence the clutch 205 are rotated, an audible sound is heard as the clutch teeth ride 203 over the clicker teeth 222.

The second driver 212 is prevented from rotating since it is splined to the clutch 205. The clicker 220 comprises a plurality of splines 221a, b. These splines 221a, b are splined to an inner surface of the inner housing 208. Therefore, when the Gap a is reduced or closed up, the second driver portion 212 cannot rotate relative to either the housing 204 or the number sleeve 206. As a consequence, the number sleeve 206 cannot rotate relative to the housing 204. If the number sleeve 206 is prevented from rotating then, as the spindle 214 is retracted back into the dose setting mechanism 200 and thereby re-set, there will be no risk of the number sleeve 206 being pushed out of the proximal side of the dose setting mechanism 200 as a result of a force being applied on the spindle 214.

Similarly, when the drug delivery device is being dispensed, the user applies an axial load to a dose button 216. The dose dial grip 202 is rotatably coupled to the dial sleeve and non-rotatably coupled to the dose button 216. The dose button 216 is axially coupled to the clutch 205 and this prevents relative axial movement. Therefore, the clutch 205 moves axially towards the cartridge end or the distal end of the dose setting mechanism 200. This movement disengages the clutch 205 from the number sleeve 206, allowing for relative rotation while closing up the Gap a.

As described above, this prevents the clutch 205 from rotating relative to the clicker 220 and hence relative to the housing 204. However, in this scenario, it also prevents the coupling between the first driver portion 210 and the second driver portion 212 from becoming disengaged. Therefore, any axial load on the spindle 214 only disengages the first and second driver portions 207, 212 when the dose button 216 is not axially loaded. This therefore does not happen during dispense.

With the dose setting mechanism 200, as a user dials a dose with the dose dial grip 202, the metal spring 201 is selected to be strong enough to maintain engagement of both clutched couplings: the clutched coupling between the clutch 205 and the number sleeve 206 and clutched coupling between the first driver portion 207 and second driver portion 212.

Figure 11:
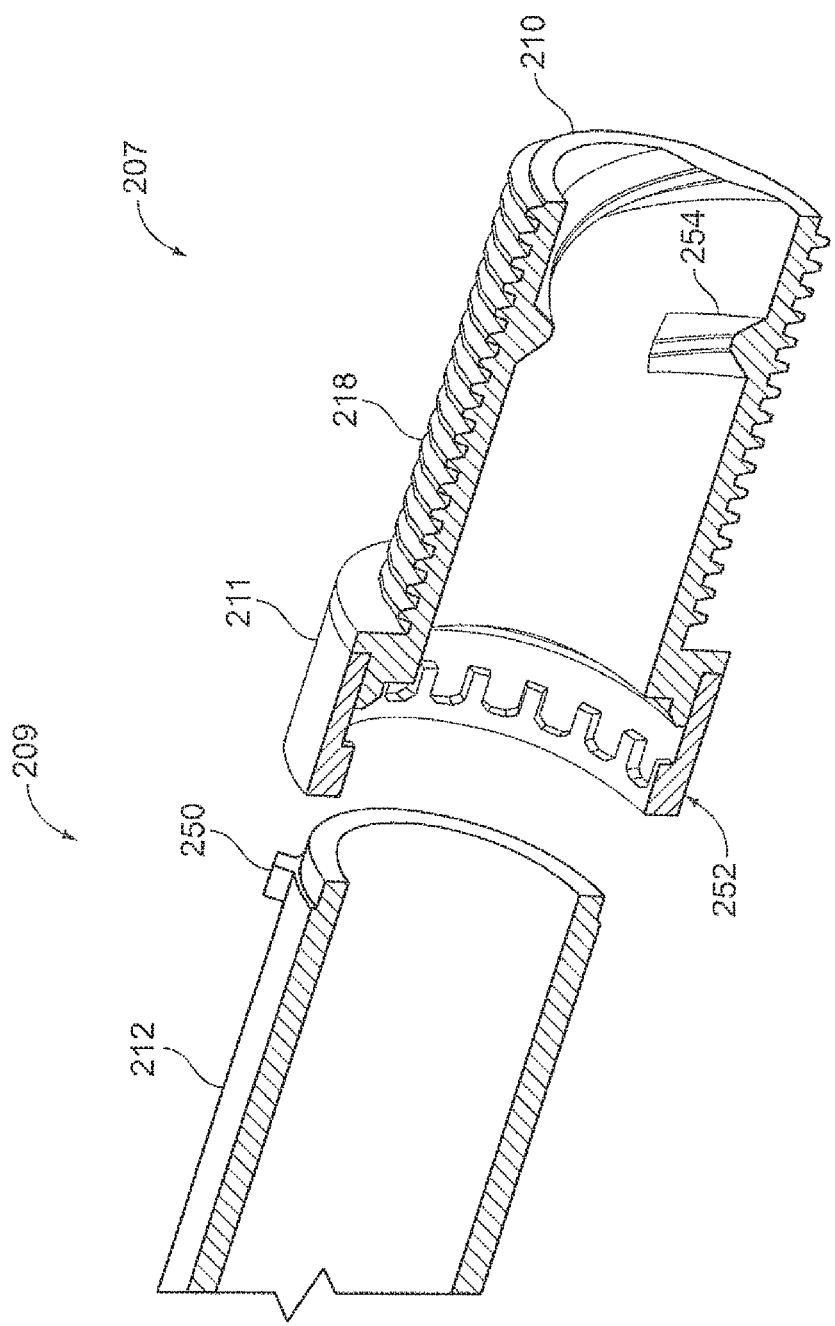
FIG. 11 illustrates a second arrangement of the driver illustrated in FIGS. 6-8 comprising a first driver portion and a second driver portion.

FIG. 11 shows in detail of a first arrangement of the first driver portion 207 and the second driver portion 212 illustrated in FIG. 8. As illustrated in FIG. 11, the second driver portion 212 is generally tubular in shape and comprises at least one drive dog 250 located at a distal end of the second driver portion 212. The first driver portion 207 also has a generally tubular shape and comprises a plurality of recesses 252 sized to engage with the drive dog 250 on the second driver portion 212. The construction of the drive dog and recesses allow disengagement with the drive dog 250 when the first and second driver portions are axially pushed together. This construction also creates a rotational coupling when these components are sprung apart. A dose limiter may be provided on first driver portion 207 and operates similarly to the dose limiter 38 illustrated in FIG. 3.

In this arrangement, the first driver portion 207 comprises a first portion 211 that is permanently clipped to a second portion 210. In this arrangement, the first portion 211 comprises the drive dogs 252 and the second component 210 includes the outer groove for the last dose nut as well as an internal groove 254. This internal groove 254 is used to connect to the spindle 214 and drives the spindle 214 during dose administration.

In the illustrated arrangement, the internal groove 254 comprises a part helical groove rather than a complete helical groove. One advantage of this arrangement is that it is generally easier to manufacture.

As may be seen from the arrangement illustrated in FIGS. 8-10 there is, in addition, certain feature enhancements over the dose setting mechanism 4 lustrated in FIGS. 3-5. These can be added independently of the ability to re-set the device to replace an empty cartridge with a new cartridge. These enhancements, therefore, are relevant to both a re-settable and non-re-settable dose setting mechanism.

One of the advantages of both arrangements illustrated but perhaps in particular in the arrangement illustrated in FIGS. 8-11 is that the dose setting mechanism 200 has a reduced number of components over other known dose setting mechanisms. In addition, apart from the metal coil spring 201 (see FIGS. 9 and 10), all of these components making up the dose setting mechanism 200 may be injection molded using inexpensive and unsophisticated tooling. As just one example, these components making up the dose setting mechanism 200 may be injection molded without the expense and sophistication of a rotating core.

Another advantage of a dose setting mechanism 200 comprising an inner housing 208 such as that illustrated in FIGS. 8-11 is that the dose setting mechanism 200 can be designed, with a slight modification, as a drug delivery device platform that is now capable of supporting both re-settable and non-resettable drug delivery devices. As just one example, to modify the re-settable dose setting mechanism 200 variant illustrated in FIGS. 8-11 into a non-resettable drug delivery device, the first driver portion 211 and 210 and the second driver portion 212 can be molded as one unitary part. This reduces the total number of drug delivery device components by two. Otherwise, the drug delivery device illustrated in FIGS. 8-11 could remain unchanged. In such a disposable device, the cartridge holder would be fixed to the housing or alternatively, made as a single one piece body and cartridge holder.

Figure 12:
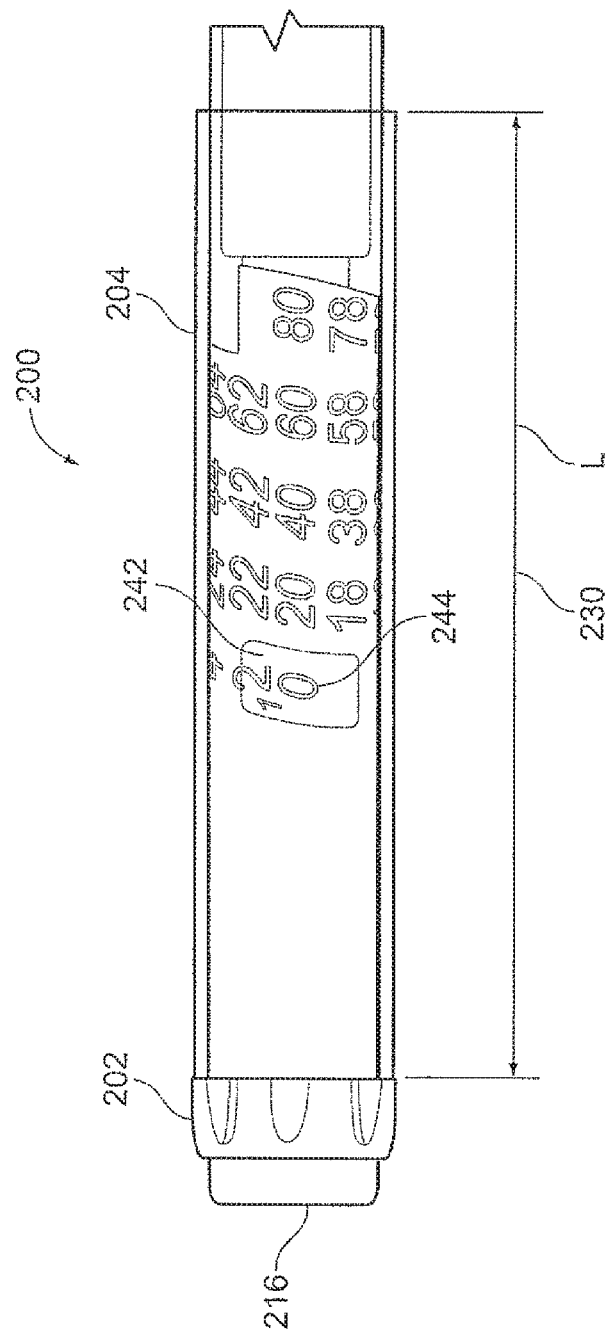
FIG. 12 illustrates the dose setting mechanism illustrated in either FIGS. 2-5 or FIGS. 6-8.

The illustration in FIGS. 8-11 shows an inner housing 208 having a length "L" 230 generally similar in overall length to the dose setting mechanism 200 (cf. FIGS. 12, 13). As will be described, providing the inner housing 208 with a length of "L" has a number of advantages over other known dose setting mechanisms that do not utilize an inner body or an inner body having a length generally equal to that of the length of a dose setting mechanism.

The inner housing 208 comprises a groove 232 provided along an external surface 234 of the inner housing. A groove guide 236 provided on an inner surface 238 of the number sleeve 206 is rotatably engaged with this groove 232.

One advantage of this dose setting mechanism 200 utilizing the inner housing 208 is that the inner housing 208 can be made from an engineering plastic that minimizes friction relative to the number sleeve 206, groove guide 236 and the groove 232. For example, one such an engineering plastic could comprise Acetal. However, those of ordinary skill in the art will recognize that other comparable engineering plastics having a low coefficient of friction could also be used. Using such an engineering plastic enables the material for the outer housing 204 to be chosen for aesthetic or tactile reasons with no friction related requirements since the outer housing 204 does not engage any moving components during normal operation.

The inner housing 208 also enables the number sleeve 206 to be provided with a helical groove guide 236 on an inner surface 238 of the number sleeve 206, rather than providing such a helical groove guide on an external surface 240 of the number sleeve 206. Providing such an internal groove guide results in a number of advantages. For example, this results in the advantage of providing more surface area along the outer surface 240 of number sleeve 206 so as to provide the scale arrangement 242. More number sleeve surface area may be used for drug or device identification purposes. Another advantage of providing the helical groove 236 on the inner surface 238 of the drive sleeve 206 is that this inner groove 236 is now protected from dirt ingress. In other words, it is more difficult for dirt to become logged in this inner groove interface than if the groove were provided along the outer surface 240 of the number sleeve 206. This feature is particularly important for a re-settable drug delivery device which will have to function over a much longer period of time compared to a non-resettable device.

The effective driving diameter (represented by 'D') of the grooved interface between the number sleeve 206 and the inner housing 208 is reduced compared to certain known drug delivery devices for the same outer body diameter. This improves efficiency and enables the drug delivery device to function with a lower pitch (represented by 'P') for this groove and groove guide connection. In other words, as the helix angle of the thread determines whether when pushed axially, the number sleeve will rotate or lock to the inner body wherein this helix angle is proportional to the ratio of P/D.

The number sleeve 206 can be made the length of the mechanism "L" 230 rather than having to split this length into the space required for the number sleeve 206 and a space required for a clicker and a dose limiter. One advantage of this configuration is that it ensures a good axial engagement between the number sleeve 206 and the outer housing 204. This improves the functionality (and perceived quality) of the dose setting mechanism when a user uses the drug delivery device to dial out a maximum settable dose. FIG. 13 illustrates the dose setting mechanism 200 dialed out to a maximum settable dose of 80 International Units ("IU").

Another advantage is that it enables the scale arrangement 242 to be hidden within the outer housing 204 even when the number sleeve 206 is fully dialed out as may be seen from FIG. 13. However, the design does not limit the position of the window 14 to that shown in FIG. 8 but allows this window 14 to be positioned at near the dose dial grip 202 of the device. In arrangements illustrated in FIGS. 12 and 13, the scale arrangement 242 will only be visible by way of the window 14.

Also the driver 209 (whether made in two portions or just one unitary component) can be made with a plain internal through hole plus a thread form that can be molded with axially moving core pins. This avoids the disadvantage of a driver having an internal thread with more than one turn and therefore requires a core pin to be rotated out several turns during a de-molding process.

One potential disadvantage of utilizing a dose setting mechanism comprising the inner housing 208 is that the use of the inner housing 208 adds a component part to the overall dose setting mechanism 200. Consequently, this inner housing 208 will tend to increase the overall wall thickness that must be designed to fit between the clutch 205 and number sleeve 206. One way to work around this design issue, as illustrated in FIG. 8, is to reduce the diameter of the clutch 205 and number sleeve 206. This in turn can be achieved because the thread form between the driver 209 and the spindle 214 comprises a male internal feature on the driver 209 and a female external groove form on the spindle 214 that are overlapping with (on a similar diameter with) the spindle groove form that interfaces with the groove along the inner surface 234 of the inner housing 208 or body portion.

The overlapping of groove forms on the spindle 214 reduces the effective diameter of the thread interface with the driver 209. This also reduces the potential outer diameter of the driver 209 enabling the addition of the inner housing 208 without increasing the overall outer diameter of the dose setting mechanism 200. Another added benefit of the reduced effective diameter of the thread interface with the driver 209 is that it improves efficiency of the drug delivery device during dispense as explained above.

The window 244 through which the scale arrangement 242 may be viewed can either be just an aperture in the outer housing 204 or can include a clear lens or window designed to magnify the scale arrangement (i.e., printed or laser marked dose numbers) along a portion of the outer surface 240 on the number sleeve 206.

The connection of a cartridge holder into the outer housing 204 can be achieved using either a screw or bayonet type connection. Alternatively, any similarly robust design used in drug delivery devices requiring a largely cylindrical part to be removed and then reattached could also be used.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A disposable drug delivery device comprising:
   a housing and a cartridge holder made as a single one piece body, the cartridge holder of the one piece body being configured to hold a cartridge;
   an inner housing received in the one piece body and comprising an external surface, the external surface defining a groove; and
   a number sleeve disposed between the one piece body and the inner housing, wherein the number sleeve has an internal surface defining a helical groove guide, wherein the number sleeve is rotatably engaged with the groove of the inner housing;
   wherein the inner housing comprises an internal surface with a mechanical configuration that is configured to prevent rotation of a driver relative to the inner housing during dispensing of a dose set by a dose setting mechanism of the drug delivery device.

2. The drug delivery device of claim 1, wherein the mechanical configuration of the inner housing comprises a spline configured to guide the driver to dispense the dose.

3. The drug delivery device of claim 1, wherein the mechanical configuration of the inner housing comprises a groove configured to guide the driver to dispense the dose.

4. The drug delivery device of claim 1, further comprising a driver and a clutch; the clutch being operatively coupled to the number sleeve and the driver, the clutch allowing the number sleeve and the driver to rotate together during a setting of a dose, and the clutch allowing relative rotation of the driver and the number sleeve during dispensing of the dose.

5. The drug delivery device of claim 1, wherein the groove defined by the external surface of the inner housing is helical and has a constant pitch.

6. The drug delivery device of claim 1, wherein the number sleeve has a smooth outer surface.

7. The drug delivery device of claim 6, comprising a scale arrangement along a portion of the smooth outer surface of the number sleeve.

8. The drug delivery device of claim 7, wherein the scale arrangement along the portion of the smooth outer surface of the number sleeve is viewable only through a window in the one piece body.

9. The drug delivery device of claim 1, further comprising a driver and a dose limiter provided between the inner housing and the driver.

10. The drug delivery device of claim 9, wherein the dose limiter is rotationally constrained to the mechanical configuration on the internal surface of the inner housing.

11. The drug delivery device of claim 9, wherein the driver comprises an external thread and wherein the dose limiter comprises an internal thread which engages the external thread of the driver.

12. The drug delivery device of claim 1, further comprising a dose dial grip configured to be rotationally coupled to the number sleeve during setting of a dose.

13. The drug delivery device of claim 1, further comprising the cartridge.

14. The drug delivery device of claim 13, wherein the cartridge contains a drug.

15. A dose setting mechanism for a drug delivery device, the dose setting mechanism comprising:
an outer housing;
an inner housing having an external groove, the inner housing having an internal surface defining a spline or a groove;
a driver;
a dial sleeve disposed between the outer housing and the inner housing, the dial sleeve being rotatably engaged with the external groove of the inner housing; and
a dose dial grip rotatably coupled to the dial sleeve,
wherein the dial sleeve and the driver are configured to rotate with respect to both the outer housing and the inner housing and are configured to translate away from both the outer housing and the inner housing when a dose is set by rotating the dose dial grip of the dose setting mechanism, and
wherein the spline or the groove of the inner housing is configured to guide the driver during dispensing of the dose set by the dose setting mechanism.

16. The dose setting mechanism of claim 15, further comprising a dose limiter disposed between the inner housing and the driver.

17. The dose setting mechanism of claim 16, wherein the dose limiter is rotationally constrained to the spline or the groove defined by the internal surface of the inner housing.

18. The dose setting mechanism of claim 16, wherein the driver comprises an external thread and wherein the dose limiter comprises an internal thread which engages the external thread of the driver.

19. A disposable drug delivery device comprising:
a housing and a cartridge holder made as a single one piece body, the cartridge holder of the one piece body being configured to hold a cartridge;
an inner housing received in the one piece body and comprising an external surface, the external surface defining a groove;
a number sleeve disposed between the one piece body and the inner housing, wherein the number sleeve has an internal surface defining a helical groove guide, wherein the number sleeve is rotatably engaged with the groove of the inner housing; and
a driver and a dose limiter provided between the inner housing and the driver;
wherein the dose limiter is rotationally constrained to a mechanical configuration on an internal surface of the inner housing.

* * * * *